(12) United States Patent
Ekpo

(10) Patent No.: US 12,144,746 B2
(45) Date of Patent: Nov. 19, 2024

(54) ORTHOPEDIC IMPLANT EXTRACTION DEVICE

(71) Applicant: Timothy Ephriam Ekpo, South Lyon, MI (US)

(72) Inventor: Timothy Ephriam Ekpo, South Lyon, MI (US)

( * ) Notice: Subject to any disclaimer, the term of this patent is extended or adjusted under 35 U.S.C. 154(b) by 409 days.

(21) Appl. No.: 17/806,596

(22) Filed: Jun. 13, 2022

(65) Prior Publication Data
US 2023/0397998 A1    Dec. 14, 2023

(51) Int. Cl.
*A61F 2/46* (2006.01)
*A61B 17/88* (2006.01)

(52) U.S. Cl.
CPC .......... *A61F 2/4603* (2013.01); *A61B 17/88* (2013.01); *A61F 2002/4619* (2013.01); *A61F 2002/4622* (2013.01)

(58) Field of Classification Search
CPC ..... A61B 17/88; A61B 17/8872; A61B 17/92; A61F 2/4603; A61F 2/461; A61F 2002/4619; A61F 2002/4622; A61F 2/4637; A61F 2002/4681
See application file for complete search history.

(56) References Cited

U.S. PATENT DOCUMENTS

| 5,732,992 A * | 3/1998 | Mauldin ................. A61F 2/461 606/205 |
| 7,879,042 B2 * | 2/2011 | Long .................... A61F 2/4609 623/22.12 |
| 8,298,241 B2 * | 10/2012 | Arnhold ................. A61F 2/461 606/99 |
| 9,089,440 B2 * | 7/2015 | Mueller ................. A61F 2/461 |

* cited by examiner

*Primary Examiner* — Larry E Waggle, Jr.
(74) *Attorney, Agent, or Firm* — Dunlap Bennett & Ludwig, PLLC

(57) ABSTRACT

A device for extracting an implant from a bone. The device has a handle that extends from a proximal end to a distal end. A pair of opposable jaws operatively associates with the distal end in such a way to move between an open position and a closed position. The first and second jaws of the pair of opposable jaws each have an arrangement of osteotome blades that align with an interfacing surface of the implant. The osteotome blades engage the jaws so as to move between a retracted position and an inserted position occupying space between the interfacing surface and the bone. A slide hammer is operatively associated with the proximal end of the handle for urging the implant linearly away from the bone with the jaws in the closed position and the osteotome blades in the inserted position.

10 Claims, 3 Drawing Sheets

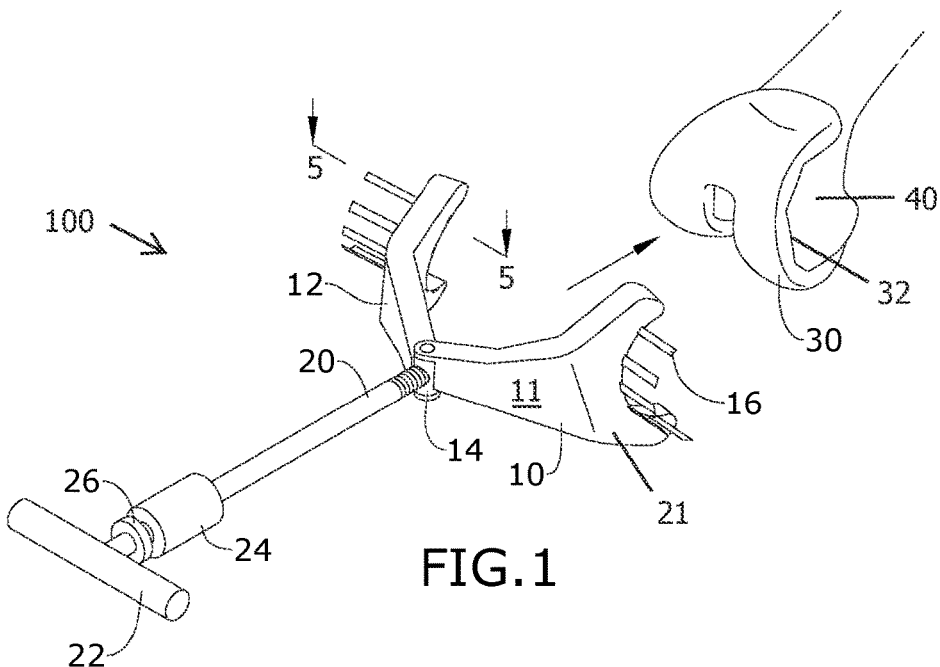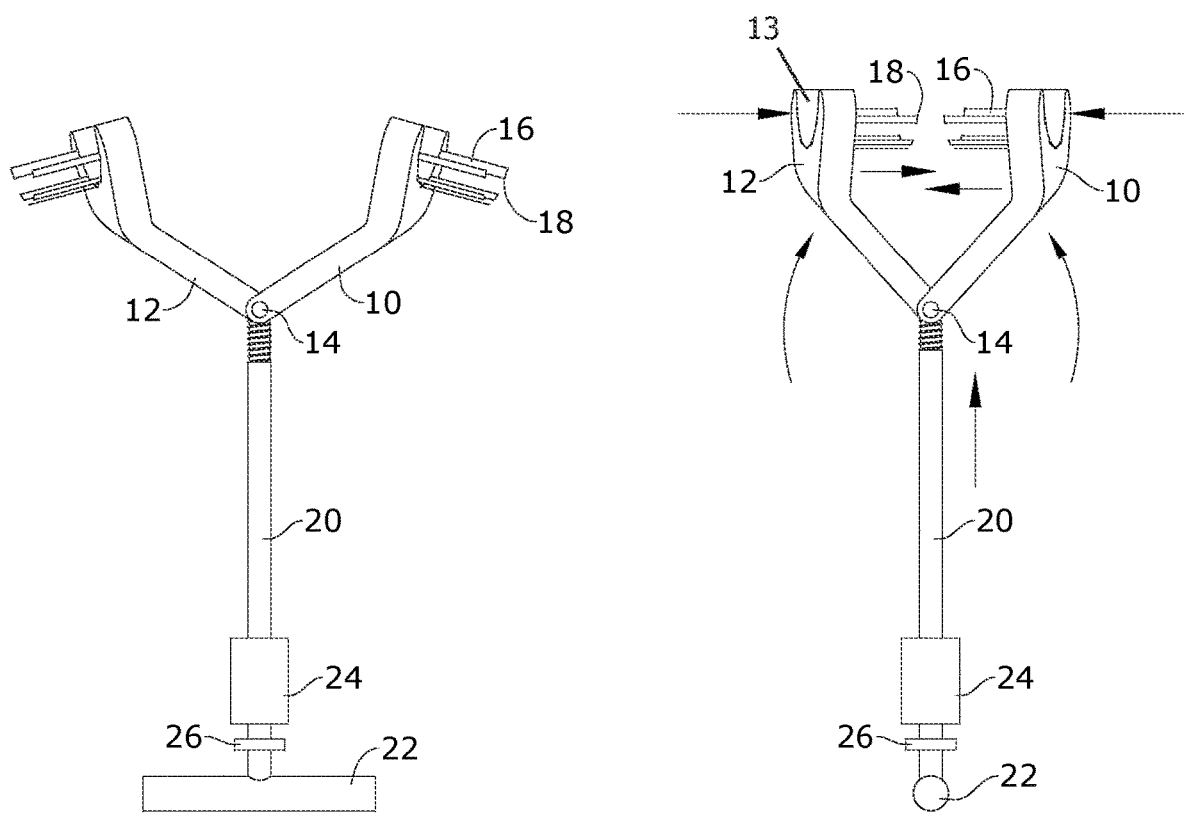

ORTHOPEDIC IMPLANT EXTRACTION DEVICE

BACKGROUND OF THE INVENTION

The present invention relates to orthopedic implants, and more particularly, to a method for orthopedic implant extraction embodied in a single instrumentation.

An orthopedic implant is a medical device manufactured to replace or to support a damaged bone. Not infrequently, a structural and functional connection forms between the living bone and the surface of the artificial implant. Typically, and adhesive or cementitious material is used to form this connection. Additionally, osseointegration growth around the implant may result at the bone-implant interface. As a result, removing the implant can be a difficult task to accomplish without major bone loss when severing the adhered joint at the bone-implant interface.

Other orthopedic implants extractors contain no blades, rather they employ manual removal, making the use of cutting devices still necessary. In other words, a hammer and mallet and chisel are used to slowly chip away at the adhesive joint prior to the attempted extraction. Thus, it is a very slow, tedious process to remove a cemented femoral implant for a revision total knee arthroplasty.

Accordingly, there is a need for a method for orthopedic implant extraction embodied in a single instrumentation. The device of the present invention includes precision osteotome blades strategically placed on a set of jaw so that after the jaw moves from an open position to a closed position, the osteotome blades move between a retracted position to an inserted position severing the adhesive joint between the implant and the bone.

The device embodied in the present invention is a single device that combines two processes (cutting and extraction) in one easy to use instrument adapted to sever the cementation and/or bony ingrowth between the bone-implant interface in concert with exerting the extraction force needed to pull the implant from the bone. The osteotome blades remove cementitious material and bony ingrowth when moving to the inserted position, wherein a handle of the device facilitates extracting the implant at same time. As a result, the device embodied in the present invention enables a user to selectively determine resection level and place.

SUMMARY OF THE INVENTION

In one aspect of the present invention, a device for extracting an implant, the implant having an interfacing surface engaging a bone, the device including: a handle; a first and second jaw opposably associated with a distal end of the handle in such a way to move between an open position and a closed position engaging opposing edges of the implant; and for each jaw, an arrangement of blades aligned with the interfacing surface in the interfacing surface in the closed position, wherein each blade of the arrangement of blades is movable between a retracted position and an inserted position, wherein the arrangement of blades occupies space between the interfacing surface and the bone.

In another aspect of the present invention, the device for extracting an implant further includes slap hammer operatively associated with the handle so as to slide between the distal end and a proximal end, wherein for each blade, a blade slot communicating opposing surfaces of the jaw, and wherein said blade is slidably associated with the blade slot, wherein for each blade has a nub on each opposing end thereof, wherein each blade slot has a nub slot on each opposing end thereof dimensioned to receive the respective nub; further including a slap stop at or near the proximal end of the handle; a manipulator extending approximately perpendicular to the proximal end of the handle, wherein each jaw provides a first portion and a second portion obtrusively angled relative to each other, wherein the second portion terminates in a conforming edge defined by a geometry that conforms or aligns with the interfacing surface; and further comprising a pivotable connection facilitating said opposable association between the first and second jaws and the distal end of the handle.

These and other features, aspects and advantages of the present invention will become better understood with reference to the following drawings, description and claims.

BRIEF DESCRIPTION OF THE DRAWINGS

FIG. 1 is a perspective view of an exemplary embodiment of the present invention, illustrating placement of an exemplary implant 30.

FIG. 2 is a top view of an exemplary embodiment of the present invention, illustrating the first and second jaws 10 and 12 in an open position and the osteotome blades 16 in a retracted position.

FIG. 3 is a top view of an exemplary embodiment of the present invention, illustrating the first and second jaws 10 and 12 in a closed position and the osteotome blades 16 in an inserted position.

DETAILED DESCRIPTION OF THE INVENTION

Figure 4:
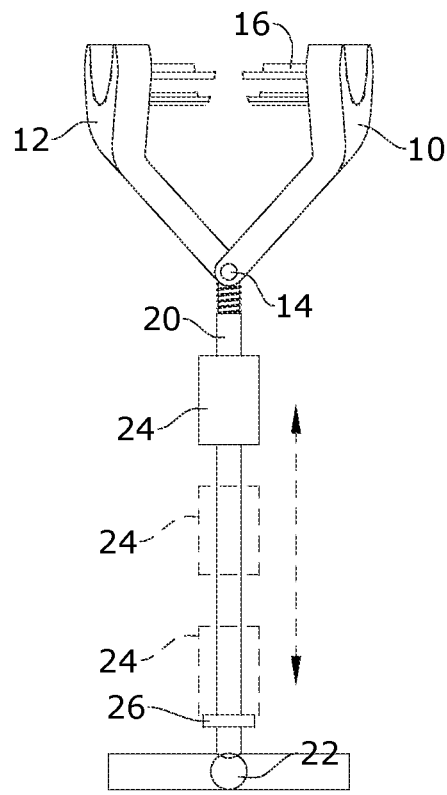
FIG. 4 is a top view of an exemplary embodiment of the present invention, illustrating the movement of a slap hammer 24.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a device for extracting an implant from a bone. The device has a handle that extends from a proximal end to a distal end. A pair of opposable jaws operatively associates with the distal end in such a way to move between an open position and a closed position. The first and second jaws of the pair of opposable jaws has an arrangement of osteotome blades that align with an interfacing surface of the implant. The osteotome blades engage the jaws so as to move between a retracted position and an inserted position occupying space between the interfacing surface and the bone. A slide hammer is operatively associated with the proximal end for urging the implant linearly away from the bone.

Referring to FIGS. 1 through 5, the present invention may include an orthopedic implant extraction device 100 and a method of using the same to remove an implant 30 from a bone 40.

Referring to FIG. 1, the implant extraction device 100 includes opposable first and second jaws 10 and 12 operatively associated to a distal end of a handle 20 so that the first and second jaws 10 and 12 are selectively movable about said distal end between an open position (FIG. 2) and a closed position (FIG. 3) for engaging opposing edges of the implant 30 targeted for extraction. Each jaw 10 and 12 may have a shape of a single-handed ice scraper, wherein a first portion 11 of the jaw and a second portion 21 of the jaw have an obtuse angular relationship relative to each other, as illustrated in the Figures.

The proximal end of the jaw operatively associates with the distal end of the handle 20 by way of an opposable connection 14 that facilitates the movement between the open and closed positions and overall inventive concept as disclosed herein. The opposable connection 14 may be, at least in part, a pivotable connection.

The second portion 21 of each jaw terminates with a conforming edge 13 that is defined by a geometry that conforms or aligns with an interfacing surface 32 of the implant 30. The interfacing surface 32 is the surface that interfaces with the bone 40, and thus is the surface of the implant 30 that needs to be pulled linearly away from the bone 40. There is likely adhesive (not shown), such as cementitious material, glue-like material, bony ingrowth, or the like that physically interconnects the implant and the bone 40, preventing the linear movement of the implant 30 relative to the bone 40.

It is to be understood that even though the Figures show a curved conforming face 13, that the conforming face 13 may be defined by a geometry that is linear, non-linear, curved, or combination thereof so long as it is dimensioned and adapted to conform/align with an adjacent portion the interfacing surface 32 of the implant 30 in the closed position. In other words, the interfacing surface 32 of the implant 30 varies depending on the implantation and the bone 40 involved.

A plurality of osteotome blades 16 may be disposed long a periphery (just inward thereof) of the conforming edge 13 on the second portion 21 of each jaw. The second portion 21 provides a plurality of blade slots 28 that communicate to opposing surfaces—the exterior surface and the interior surface—of the second portion 21. The interior surfaces of the two opposable jaws 10 and 12 are facing each other, as illustrated in FIG. 3, while the exterior surfaces of the two opposable jaws 10 and 12 are facing away from each other. The blade slots 28 may be spaced apart or may be one or more continuous slots, which facilitates the disclosure herein. Each blade slot 28 slidable receives a respective osteotome blade 16 in such a way that the osteotome blade 16 is movable between a retracted position (where the osteotome blade 16 protrudes from the exterior surface, as illustrated in FIG. 2) and an inserted position (where the osteotome blade 16 protrudes from the interior surface, as illustrated in FIG. 3).

Figure 5:
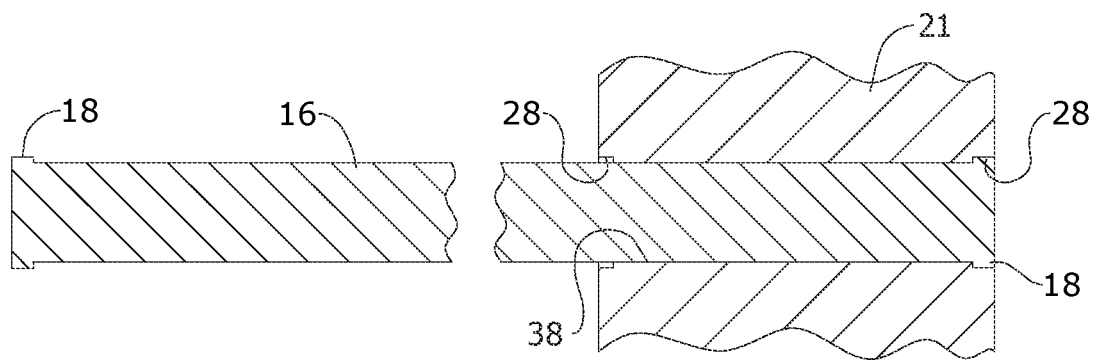
FIG. 5 is a detailed section view of an exemplary embodiment of the present invention, taken along line 5-5 of FIG. 1.
Figure 6:
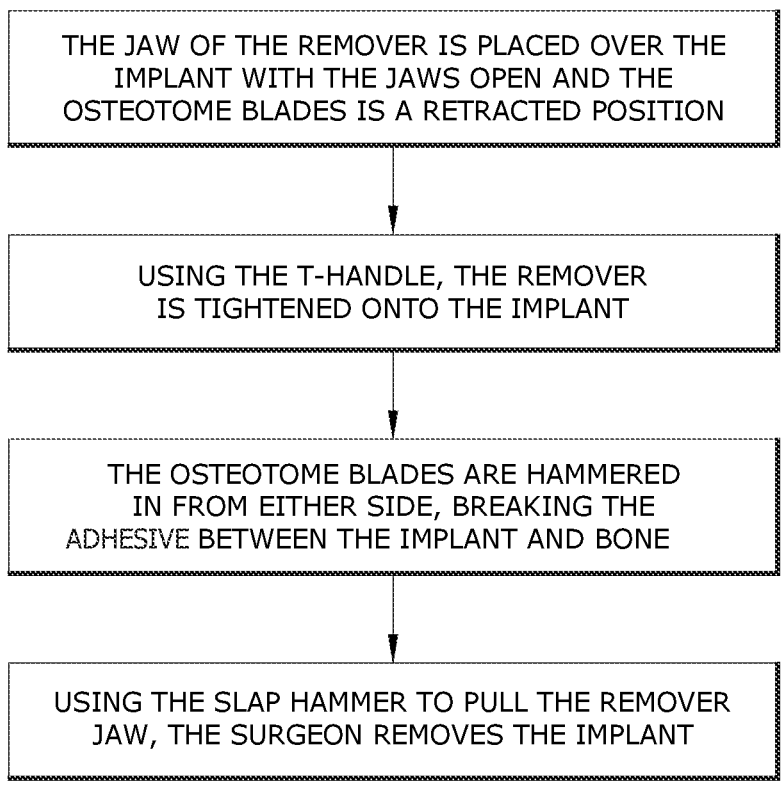
FIG. 6 is a flow chart of an exemplary embodiment of the present invention.

Referring to FIG. 5, each osteotome blade 16 may have blade nubs 18 or circumferential or peripheral protrusions/flanges on each end. Each blade slot 28 may have one or more nubs slot 38 dimensioned and adapted to receive the blade nubs 18 preventing the osteotome blade 16 from sliding out of the blade slot 28 in either the retracted or the inserted position.

Referring to FIG. 4. a slap hammer 24 may be operatively associated to and exterior of the handle 20 so that the slap hammer 24 slidably moves between the distal and proximal ends of the handle 20. A proximal end of the handle 30 may have a slap stop 26 for engaging the sliding slap hammer 24 during the hammering process, thereby urging the handle 30 and thus the connected jaws 10 and 12 in the proximal direction colinear with the movement of the slap hammer moving from the distal end of the handle 30 to its proximal end. The proximal end may provide manipulators 22 for a user to manipulate.

A method of using the present invention includes the following. The implant extraction device 100 disclosed above is provided with the jaws 10 and 12 in the open position and the osteotome blade 16 in the retracted position. A user, such as an orthopedic surgeon, may manipulate the manipulators 22 to move the jaws 10 and 12 against the implant 30—against a front face and two opposing side faces of the implant 30. The jaws are then moved to the closed position, which in turn effectuates a nested condition, wherein the implant 30 nests in the cupped jaws 10 and 12. In the nested condition, the conforming face 13 aligns with the interfacing surface 32 of the implant 30. The osteotome blades 16 are moved from the retracted position to the inserted position, in certain embodiments by way of a driving device, such as a hammer, thereby the osteotome blades 16 are urged between the implant 20 and bone 40 along the interfacing surface 32, breaking through any adhesive. The slap hammer 24 is employed to extract the implant 30, pulling it away from the bone 40. For instance, an orthopedic surgeon would use the present invention for safe and effective removal of a femoral component from the femur in revision total knee arthroplasty.

Additionally, because these knee implants come in different sizes, the device described will likely come in a few sizes-extra small, small, standard, large and extra-large. As well as embodiments with one handle and multiple jaws, wherein the handle is interchangeable with any of the jaws.

As used in this application, the term "about" or "approximately" refers to a range of values within plus or minus 10% of the specified number. And the term "substantially" refers to between 90% to 110% of more of an entirety or an extent it the term references. Recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the disclosed embodiments.

In the following description, it is understood that terms such as "first," "second," "top," "bottom," "up," "down," and the like, are words of convenience and are not to be construed as limiting terms unless specifically stated to the contrary.

It should be understood, of course, that the foregoing relates to exemplary embodiments of the invention and that modifications may be made without departing from the spirit and scope of the invention as set forth in the following claims.

What is claimed is:

1. A device for extracting an implant, the implant having an interfacing surface engaging a bone, the device comprising:

a handle;

a first and second jaw opposably associated with a distal end of the handle in such a way to move between an open position and a closed position engaging opposing edges of the implant; and for each jaw, an arrangement of blades is aligned with the interfacing surface in the closed position, wherein each blade of the arrangement of blades is movable between a retracted position and an inserted position, wherein the arrangement of blades occupies space between the interfacing surface and the bone.

2. The device of claim 1, further comprising a slap hammer operatively associated with the handle so as to slide between the distal end and a proximal end.

3. The device of claim 2, wherein for each blade, a blade slot communicates with opposing surfaces of the jaw, and wherein said blade is slidably associated with the blade slot.

4. The device of claim 3, wherein each blade has a nub on each opposing end thereof.

5. The device of claim 4, wherein each blade slot has a nub slot on each opposing end thereof dimensioned to receive the respective nub.

6. The device of claim 5, further comprising a slap stop at or near the proximal end of the handle.

7. The device of claim 6, further comprising a manipulator extending approximately perpendicular to the proximal end of the handle.

8. The device of claim 7, wherein each jaw provides a first portion and a second portion obtrusively angled relative to each other.

9. The device of claim 8, wherein the second portion terminates in a conforming edge defined by a geometry that conforms or aligns with the interfacing surface.

10. The device of claim 9, further comprising a pivotable connection facilitating said opposable association between the first and second jaws and the distal end of the handle.

* * * * *